United States Patent
Häupl

(10) Patent No.: US 7,497,616 B2
(45) Date of Patent: Mar. 3, 2009

(54) MOUNT FOR IMAGE RECEIVER

(75) Inventor: Rainer Häupl, Krummennaab (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/649,140

(22) Filed: Jan. 3, 2007

(65) Prior Publication Data

US 2007/0195937 A1   Aug. 23, 2007

(30) Foreign Application Priority Data

Jan. 16, 2006   (DE) .................. 10 2006 002 083

(51) Int. Cl.
*H01J 31/49* (2006.01)
*H05G 1/64* (2006.01)

(52) U.S. Cl. .................. 378/189; 378/98.8

(58) Field of Classification Search .......... 378/19, 378/20, 98.8, 167–169, 176–180, 189–192, 378/208, 209

See application file for complete search history.

(56) References Cited

U.S. PATENT DOCUMENTS

| | | | |
|---|---|---|---|
| 4,905,269 A | | 2/1990 | Mosby |
| 4,943,991 A | | 7/1990 | Mosby |
| 5,313,066 A | * | 5/1994 | Lee et al. ............... 250/370.09 |
| 5,555,284 A | * | 9/1996 | Kishigami ................... 378/177 |
| 6,152,598 A | * | 11/2000 | Tomisaki et al. ............ 378/209 |
| 6,181,769 B1 | * | 1/2001 | Hoheisel et al. ............ 378/98.8 |
| 6,982,424 B2 | * | 1/2006 | Vafi et al. ............... 250/370.11 |
| 2004/0028176 A1 | * | 2/2004 | Kamenetsky et al. ......... 378/37 |

FOREIGN PATENT DOCUMENTS

| | | |
|---|---|---|
| DE | 102 44 177 | 4/2004 |
| EP | 0 189 710 | 1/1989 |
| EP | 0 908 743 | 7/2006 |

OTHER PUBLICATIONS

German Office Action dated Oct. 4, 2007 for DE 10 2006 002 083. 9-52 with English translation.

* cited by examiner

*Primary Examiner*—Irakli Kiknadze
(74) *Attorney, Agent, or Firm*—Brinks, Hofer, Gilson & Lione

(57) ABSTRACT

A mount for an image receiver is provided. The mount includes at least two opposite edges that include a section with a curved contour. At least one of the sections of the mount is curved concavely. The concave curvature enables the use of a mount for x-ray lung radiographs or mammographs. The section may also be embodied as a concave-convex section.

9 Claims, 2 Drawing Sheets

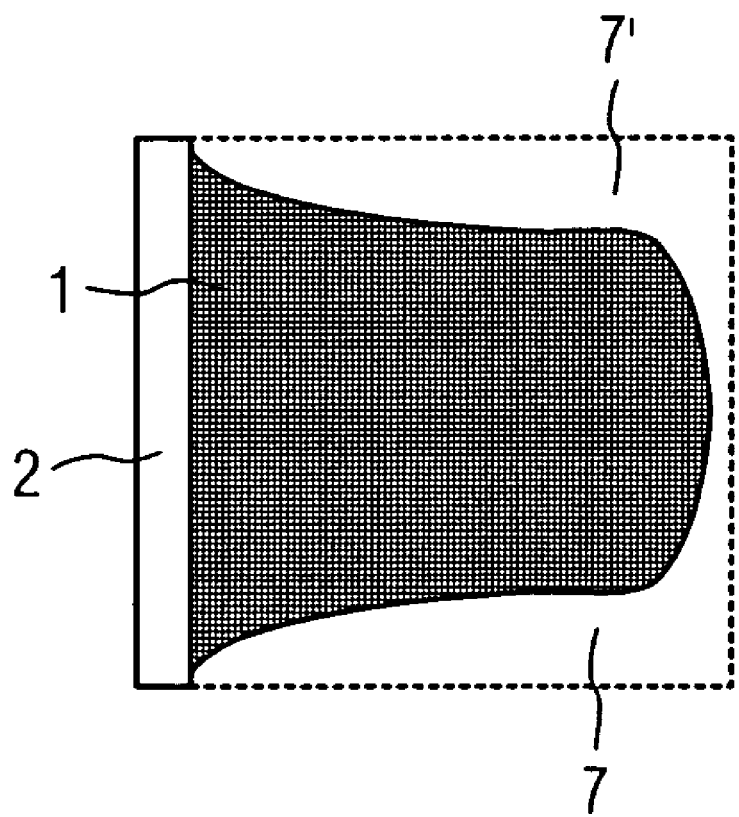

MOUNT FOR IMAGE RECEIVER

The present patent document claims the benefit of the filing date of DE 10 2006 002 083.9 filed Jan. 16, 2006, which is hereby incorporated by reference.

BACKGROUND

The present embodiments relate to a mount for an image receiver.

Mounts for image receivers includes a casing, which encapsulates, for example, an x-ray detector, a scattered radiation grid and an exposure timer. Mounts for x-ray detectors may be used in x-ray diagnostic devices for medical purposes. Other types of image receivers may be supported on mounts, for example, gamma detectors.

Generally, x-ray detectors available on the market include a square or rectangular shape. X-ray films with intensifying screens and phosphor systems generally have a rectangular shape. The solid body matrix detectors described in EP 0 189 710 and made from cesium iodide (CsI) and amorphous silicon (a-Si) or, as described in U.S. Pat. No. 5,313,066, made from selenium (Se) and a-Si, have a rectangular, square form. Accordingly, they are supported by rectangular mounts.

Digital x-ray detectors usually include a matrix of detector elements, which are controlled and read out by way of a line-column-based electronics system. A register readout includes lines or columns that are constructed as registers. DE 102 44 177 discloses a reverse-side arrangement of the control elements instead of a peripheral line-column-based arrangement. Using the reverse-side arrangement there is no need to provide the border areas of the detector for the electronics system. For example, this arrangement allows x-ray detectors to be developed with contours other than rectangular contours.

X-ray recording system produce x-ray recordings of the human body. It is desirable to be able to get as close as possible to the human body with the x-ray recording system. With mammographs, for example, the tissue near the chest wall is examined. With chest radiographs, the neck of the patient is also imaged. The existing x-ray recording systems and their formats are not sufficiently adequate to examine the chest wall using chest radiographs.

X-ray recording systems are constructed such that the surface sensitive to x-rays on one side reaches as close as possible to the edge of the image receiver. On this side, in a mammography diagnostic device, for example, the distance from the x-ray film in the film-screen-cassette to the chest wall amounts to a few millimeters when the mount is of a suitable design.

EP 0 908 743 discloses an x-ray recording system having an x-ray detector. The matrix of the areas serving the imaging projects are positioned as near as possible to the body of the person to be examined, so that examinations of points that are difficult to reach are also possible. One of the sides of the x-ray detector is a section with a curved contour, so that the x-ray detector may be adjusted to the anatomic factors, and may be immediately adducted towards the body of a patient.

By using the x-ray detector disclosed in EP 0 908 743, lung radiographs, for example, may be created. The x-ray detector is supported on a mount, which features a "chin depression" on its above-lying edge. The curved section of the x-ray detector is adjusted to the chin depression and rests against this on the inside of the mount. The patient places his/her chin into this depression. In this arrangement, the distance from the active surface of the x-ray detector to the examination point is kept to a minimum. Also in this arrangement, the patient is able to be centered with respect to the x-ray detector.

As disclosed in EP 0 908 743, the positioning of the x-ray detector to the x-ray emitter is restricted because the chin depression must be arranged above so that the patient can place his/her chin inside. For example, the x-ray detector may be rotated about 180° so that the active surface can lie on the opposite side. With this rotation, the chin depression is arranged on the lower lying edge of the x-ray detector, so that at least one lung radiograph is no longer expediently possible, because the patient is unable to place his/her chin into the chin depression from below.

SUMMARY

The present embodiments may obviate one or more of the limitations or draw-backs inherent in the related art. For example, in one embodiment, a mount for an image receiver includes an improved, less restricted positioning ability.

In one embodiment, a mount for an image receiver has at least two opposite edges, which include a section with a curved contour. The mount for imaging applications, which require a curved contour, can be rotated at least in one direction about 180°, without the curved section subsequently being incorrectly oriented. This embodiment, for example, results in a direction-invariant contour of the mount.

In one embodiment, at least one of the sections of the mount is curved concavely. A concave curvature enables the use of the mount for lung radiographs because the section serves as a chin depression, or the mount is used for mammographs.

In one embodiment, the mount comprises a symmetrical contour. In this embodiment, the mount to be used in an orientation-invariant manner in respect of the respective symmetry, i.e. the respective section of the x-ray detectors, likewise remains independent of the orientation.

BRIEF DESCRIPTION OF THE DRAWINGS

FIG. 3 illustrates one embodiment of a mount for an image receiver with a two-sided concavely-convexly curved section.

DETAILED DESCRIPTION

Figure 1:
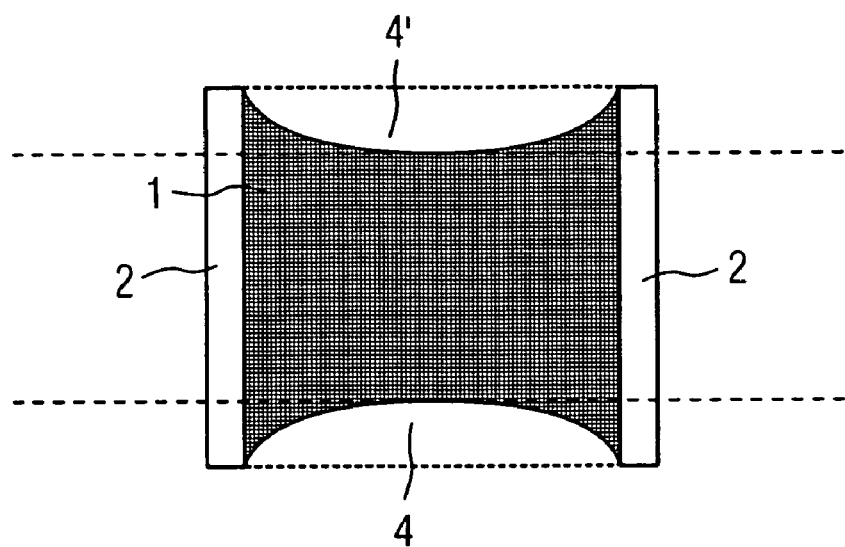
FIG. 1 illustrates one embodiment of a mount for an image receiver with a two-sided concavely curved section.

FIG. 1 illustrates one embodiment of a mount 1 for an image receiver, for example, an x-ray detector.

An x-ray detector may be manufactured by affixing photodiodes, switching elements (i.e. thin film transistors or switching diodes) and conductors to a rectangular glass substrate using thin film deposition techniques and photolithographic structuring, such that they form a matrix-shaped array of n rows and m columns of image elements. The photodiodes may be manufactured from amorphous silicon (a-Si).

In one embodiment, the x-ray detector supported on the mount 1 includes a non image-active region, which effects a non image-active region 2 of the mount 1. The non image-active region of the x-ray detector may include, for example, mechanical or electrical components.

The x-ray detector is supported by and encapsulated in a mount 1. A section 4, 4' with a concavely curved contour is provided on the above-lying and below-lying side of the mount 1. This contour of the curved section 4 may be adjusted to the anatomy of the body part of an average patient to be examined. The x-ray detector likewise includes concave sections, with which it rests on the inside against the concave sections 4, 4' of the mount.

The curved sections are produced, for example, by shaping components.

Figure 2:
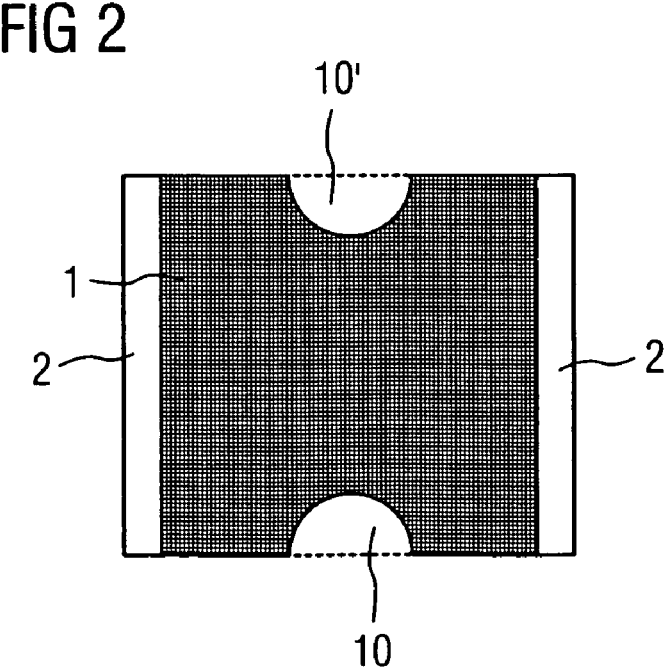
FIG. 2 illustrates one embodiment of a mount for an image receiver with a two-sided chin depression.

FIG. 2 shows a mount 1 for an image receiver which is comparable to the embodiment shown in FIG. 1. The concavely curved sections are however designed as chin depressions 10, 10', the curvature of which comprises a smaller radius than that illustrated in FIG. 1.

FIG. 3 shows a mount 1 for an image receiver which is comparable to that shown in FIG. 1. However, it comprises a concave-convex section 7, 7' instead of concave sections.

Only mirror-symmetrical contours of the mount 1 have been explained. Depending on the intended application, point-symmetrical or asymmetrical contours may also be used.

The present embodiments relate to a mount 1 for an image receiver, in particular an x-ray detector. In one embodiment, at least two opposite edges of the mount 1 include a section with a curved contour. The mount 1 for x-ray imaging applications, which requires a curved contour, may be rotated about 180°, without the curved section being subsequently incorrectly oriented. This embodiment results in a direction-invariant contour of the mount 1. In one embodiment, at least one of the sections of the mount is curved concavely. A concave curvature particularly enables the use of a mount for x-ray lung radiographs in that the section serves as a chin depression or the mount is used for mammographs.

The invention claimed is:

1. A mount for an image receiver, comprising:
 a first edge, and
 a second edge that is opposite the first edge,
 wherein the first edge comprises a first section with a first curved contour sized and shaped as a first chin depression, and the second edge comprises a second section with a second curved contour sized and shaped as a second chin depression.

2. The mount as claimed in claim 1, wherein at least one of the first or second sections comprises a concave curve.

3. The mount as claimed in claim 1, wherein at least one of the first or second sections comprises a symmetrical contour.

4. The mount as claimed in claim 1, further comprising a digital x-ray detector connected with the mount.

5. The mount as claimed in claim 1, wherein the mount is structured to support an x-ray detector.

6. The mount as claimed in claim 1, wherein the mount is operable for use in x-ray chest examinations.

7. The mount as claimed in claim 1, further comprising a third edge, wherein the third edge comprises a third section with a third curved contour.

8. The mount as claimed in claim 1, wherein the first section and second section are concave sections and the third section is a convex section.

9. The mount as claimed in claim 1, wherein the first edge and second edge may be rotated about 180°.

* * * * *